(12) United States Patent
Meyer et al.

(10) Patent No.: US 7,867,260 B2
(45) Date of Patent: Jan. 11, 2011

(54) PLATE USED TO STABILISE DISTAL RADIUS FRACTURES

(75) Inventors: Olaf Meyer, Neu Zittau (DE); Arnd Ehrhardt, Koenigsee (DE); Ulrich Dankwerth, Berlin (DE); Ulrich Finger, Saalfeld (DE)

(73) Assignee: Koenigsee Implantate und Instrumente zur Osteosynthese GmbH, Koenigsee-Aschau (DE)

( * ) Notice: Subject to any disclaimer, the term of this patent is extended or adjusted under 35 U.S.C. 154(b) by 647 days.

(21) Appl. No.: 10/578,567

(22) PCT Filed: Nov. 2, 2004

(86) PCT No.: PCT/EP2004/012385

§ 371 (c)(1),
(2), (4) Date: Dec. 15, 2006

(87) PCT Pub. No.: WO2005/044122

PCT Pub. Date: May 19, 2005

(65) Prior Publication Data

US 2007/0123886 A1     May 31, 2007

(30) Foreign Application Priority Data

Nov. 5, 2003  (DE) ............................... 103 51 501
Dec. 5, 2003  (DE) ............................... 103 56 904

(51) Int. Cl.
    *A61F 2/30*    (2006.01)
(52) U.S. Cl. .......................................... 606/280; 606/70
(58) Field of Classification Search ............. 606/70–71, 606/280–299
See application file for complete search history.

(56) References Cited

U.S. PATENT DOCUMENTS

| | | | | |
|---|---|---|---|---|
| 4,923,471 | A | * | 5/1990 | Morgan ........................ 606/60 |
| 5,015,248 | A | * | 5/1991 | Burstein et al. ............... 606/74 |
| 5,197,966 | A | * | 3/1993 | Sommerkamp ............. 606/286 |
| 5,275,601 | A | * | 1/1994 | Gogolewski et al. ........ 606/291 |
| 5,674,222 | A | * | 10/1997 | Berger et al. .................. 606/71 |
| 5,779,706 | A | * | 7/1998 | Tschakaloff ................. 606/281 |
| 5,827,286 | A | * | 10/1998 | Incavo et al. .................. 606/71 |
| 5,931,839 | A | * | 8/1999 | Medoff ....................... 606/286 |
| 6,096,040 | A | * | 8/2000 | Esser .......................... 606/280 |
| 6,206,881 | B1 | * | 3/2001 | Frigg et al. .................. 606/291 |
| 6,283,969 | B1 | * | 9/2001 | Grusin et al. ............... 606/280 |
| 6,623,486 | B1 | * | 9/2003 | Weaver et al. ............... 606/281 |
| 6,890,335 | B2 | * | 5/2005 | Grabowski et al. ............ 606/71 |

(Continued)

FOREIGN PATENT DOCUMENTS

DE          101 25 092        12/2001

(Continued)

*Primary Examiner*—Thomas C Barrett
*Assistant Examiner*—Matthew Lawson
(74) *Attorney, Agent, or Firm*—Oblon, Spivak, McClelland, Maier & Neustadt, L.L.P.

(57) ABSTRACT

A plate for stabilizing distal radius fractures, comprising a longitudinal shaft with an adjacent distal, anatomically preformed plate part, with the envelope of the plate part having an essentially triangular shape, and threaded bores with longitudinal axes arranged in both the shaft and the distal plate part and being cone-like at least at the distal plate end, which extend in a predominately non-parallel manner in the distal plate part, and wherein a bend is formed between the shaft and the plate part.

18 Claims, 3 Drawing Sheets

U.S. PATENT DOCUMENTS

Figure 1:
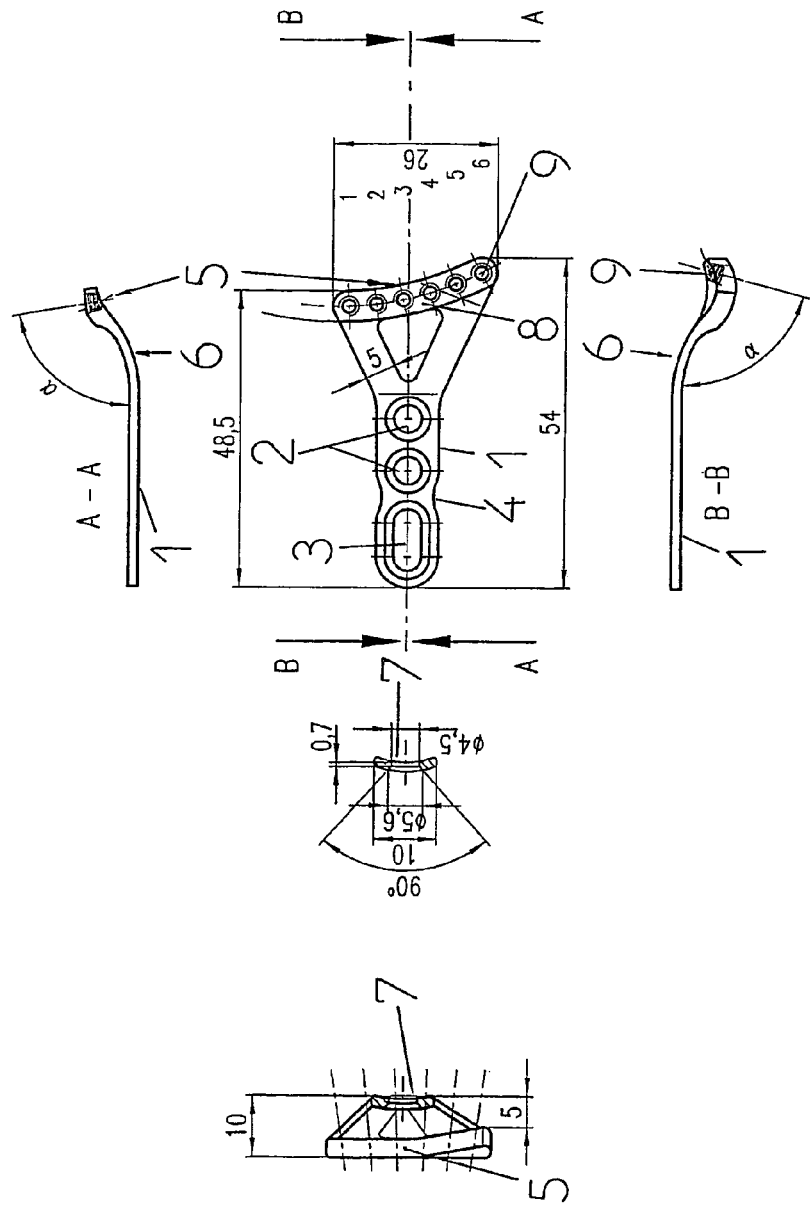
Figure 1:
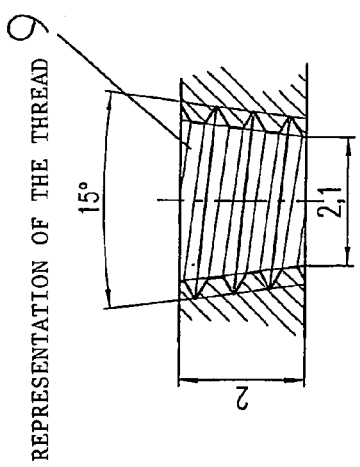

| | | |
|---|---|---|
| 7,179,260 B2 * | 2/2007 | Gerlach et al. .............. 606/291 |
| 7,335,204 B2 * | 2/2008 | Tornier ....................... 606/284 |
| 7,354,441 B2 * | 4/2008 | Frigg ......................... 606/261 |
| 2002/0045901 A1 * | 4/2002 | Wagner et al. ................ 606/69 |
| 2004/0102778 A1 * | 5/2004 | Huebner et al. .............. 606/71 |
| 2004/0210220 A1 * | 10/2004 | Tornier ....................... 606/69 |
| 2004/0267261 A1 * | 12/2004 | Derouet ....................... 606/70 |
| 2005/0010225 A1 * | 1/2005 | Del Medico ................ 606/69 |
| 2006/0217722 A1 * | 9/2006 | Dutoit et al. .................. 606/69 |

FOREIGN PATENT DOCUMENTS

| | | | |
|---|---|---|---|
| DE | 203 09 361 | | 9/2003 |
| EP | 0 723 764 | | 7/1996 |
| WO | WO 00/53110 | * | 7/2000 |
| WO | WO 01/19267 | * | 3/2001 |
| WO | 03/007832 | | 1/2003 |

* cited by examiner

REPRESENTATION OF THE THREAD

PLATE USED TO STABILISE DISTAL RADIUS FRACTURES

The invention relates to a plate for stabilizing distal radius fractures, comprising a longitudinal shaft with an adjacent distal, anatomically preformed plate part, with the envelope of the plate part having an essentially triangular shape, and round holes arranged in both the shaft and the distal plate part, which may be threaded bores with a cone-like shape, with threaded longitudinal axes extending in a predominately non-parallel manner in the distal plate part, and wherein a right-angle bend is formed between the shaft and the plate part, according to the preamble of patent claim 1.

Distal radius fractures, which are fractures of the radius portion proximal to the wrist, mostly due to a fall onto the extended or flexed hand, are the most frequent bone injuries with human beings. The radius mainly breaks near the wrist, with or without participation of the joint surface. Bad injuries with fractures of the actual joint surface are usually the result of forces acting axially onto the wrist, which—in the extreme case—split the radius into several fragments. Such fractures relate to patients performing types of sport like, for instance, inline skating, motorcycling or snow boarding.

The operation indication depends on the type of the fracture and the extent of the dislocation. Volar flexion or Smith's fractures are always instable and an indication of a volar support plate osteosynthesis. A dorsal and/or radial comminuted zone involves the danger that the fragments tilt even after the reduction. Here, too, there exists an operation indication. To avoid a secondary dislocation, also volar fixed-angle plates are preferably used.

Such a fixed-angle plate for the distal radius fracture comprising an anatomically preformed distal plate part is prior art and goes back, for example, to Königsee Implantate und Instrumente zur Osteosynthese GmbH. With the so-called plate according to Dr. Petereit for the volar application the operative reduction result is permanently fixed by three fixed-angle screws, and no intraoperative corrections are required. This known fixed-angle plate for the distal radius fracture comprises a longitudinal shaft and a distal plate part, with the shaft and the plate part being connected by a right-angle bend. The essentially triangular distal plate part receives the aforementioned fixed-angle screws. To this end, conical threaded bores are formed in the plate part. However, due to its very rigid configuration this known plate does not allow an intra-operative remodeling. In the case of a dorsal and/or radial comminuted zone the plates according to the prior do not always, and not without problems, allow to secure all fragments after the reduction, which constitutes a further drawback.

Based on the foregoing it is, therefore, the object of the invention to provide a further developed new plate for stabilizing distal radius fractures, comprising a longitudinal shaft with an adjacent distal, anatomically preformed plate part, wherein the plate to be provided basically allows a reduction of the operation trauma and has a very high functionality. The plate itself is to allow a remodeling thereof by the operator and is to offer the possibility to fix at a fixed angle even complicated fractures with several fragments after the reduction.

The solution to the object of the invention is achieved with a fixed-angle plate according to the features of patent claim 1, wherein the dependent claims define at least useful embodiments and advancements.

According to the basic gist of the invention the triangular shape of the plate part or the respective envelope of this plate part is scalene. The side of the triangle or the envelope, respectively, away from the shaft comprises a plurality of conical threaded bores, wherein the bore diameter of these threaded bores is chosen to be substantially smaller than the diameter of the threaded bores in the shaft.

The threaded longitudinal axes of the plurality of the bores in the distal plate part include predominately different angles $\alpha$ toward the shaft part, which deviate from 90°.

According to a preferred embodiment the side of the triangle away from the shaft comprises a discontinuance or free surface, with the shaft and the plate part forming a Y-shape.

According to this embodiment a transverse-surface section is provided on the respective sides of the plate part co-forming the Y-shape, each comprising at least two conical threaded bores. The transverse-surface sections may vary in length and/or width and may be angled or offset, respectively with respect to the shaft part.

Beside conical threaded bores for receiving fastening screws the shaft is provided with an oblong hole so as to facilitate by this combination an alignment of the plate, and to ensure, on the other hand, a secure fixation by the screws.

The cross-sectional area of the shaft preferably has a vault to minimize irritations of the bone surface.

For the purpose of the optimized anatomic adaptation of the radius plate the corner points of the triangular distal plate part are not located on a plane surface, but such a plate structure is conceivable where the corner points of the triangular plate part are located on a curved surface.

According to an embodiment of the plate for stabilizing distal radius fractures, especially of a volar plate, the threaded bores in the plate part are placed on the side of the triangle away from the shaft, namely in an arcuate arrangement.

The shaft of the radius plate may be waisted. This waisted shape is preferably provided in the region between the aforementioned oblong hole and the larger diameter fixing bore adjacent thereto.

According to one embodiment of the invention the diameter of the bore of the threaded bores in the distal plate part is chosen to be smaller by approximately half the diameter of the screw holes in the shaft of the plate.

Especially with an embodiment of the radius plate in a Y-shape can an easy remodeling of the Y-legs and/or the transverse-surface sections at the ends of the legs be performed.

In contrast to conventional plates the aforementioned Y-shape has, in dorsal use, the advantage that the tuberculum listeri need not be removed, so that the operation trauma can be reduced.

Possible multi-fragment fractures can very well be fixed especially by choosing fixed-angle screws having a diameter of substantially 2 mm. Four to eight, preferably five or six screws having a cortical thread in the screw shaft are used.

The plate itself is fabricated from implant materials known per se, especially implant steel or titanium, or from titanium alloys, respectively.

The invention will be explained in more detail by means of embodiments and figures below.

IN THE DRAWINGS

Figure 2:
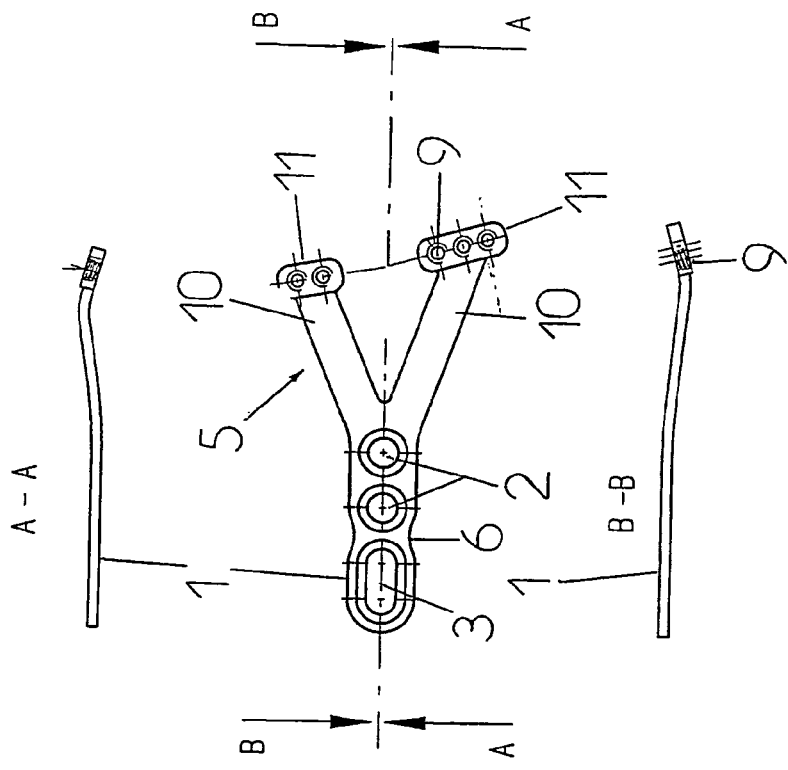
Figure 2:
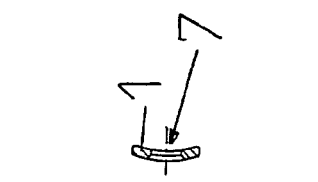
Figure 2:
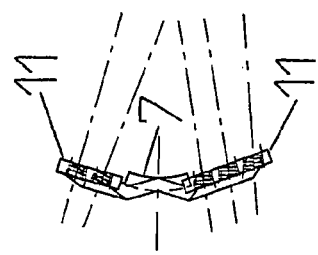
Figure 2:
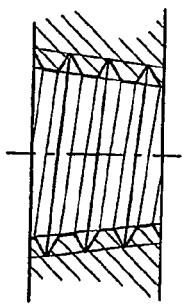

FIG. 1 shows different views of a volar radius plate with closed legs in the distal plate part, and FIG. 2, 3 show views of a Y-shaped radius plate with a resulting open configuration in the area of the distal plate part.

As can be seen from the figures, the distal radius plate comprises a longitudinal shaft 1 including an arrangement of screw holes with or without conical threaded bores 2 in combination with an oblong hole 3. In the transition area between the oblong hole 3 and the adjacent screw hole 2 a symmetrical waist-shaped recess 4 is provided in the shaft.

A right-angle bend 6 is provided in the transition area from the shaft 1 to the distal plate part 5, so that the desired basic structure corresponding to the anatomic conditions is achieved.

As can be seen from the figures, the cross-section of the shaft 1 is provided with a vault 7 which helps to avoid irritations of the bone skin.

In the embodiment of FIG. 1 a scalene triangular shape of the plate part 5 is assumed.

The side of the triangle away from the shaft 1, i.e. side 8, comprises a plurality of conical threaded bores 9 with a smaller diameter than the diameter of the screw holes 2 in the shaft 1.

The course of the conical bores 9 having a smaller diameter in the distal plate part 5 extends approximately on a curved line.

The threaded longitudinal axes of the plurality of the bores in the plate part 5 are positioned at different angles α toward the plate part, wherein α has a value deviating from 90°. The designation of the bores provided with numerals 1 to 6 has the angle dimensions indicated in the figure, in the range from 60° to 89°.

The front face view of the plate according to FIG. 1 with the recognizable distal plate end demonstrates that the corner points of this approximately triangular plate part do not lie on a plane surface, but on a curved one adapted to the anatomical conditions. The representation of the thread according to FIG. 1 relates to the plurality of threaded bores in the distal plate part 5, wherein the necessary fixed angle results from the conical configuration when screwing in a screw with a complementary thread in the screw head.

Figure 3:
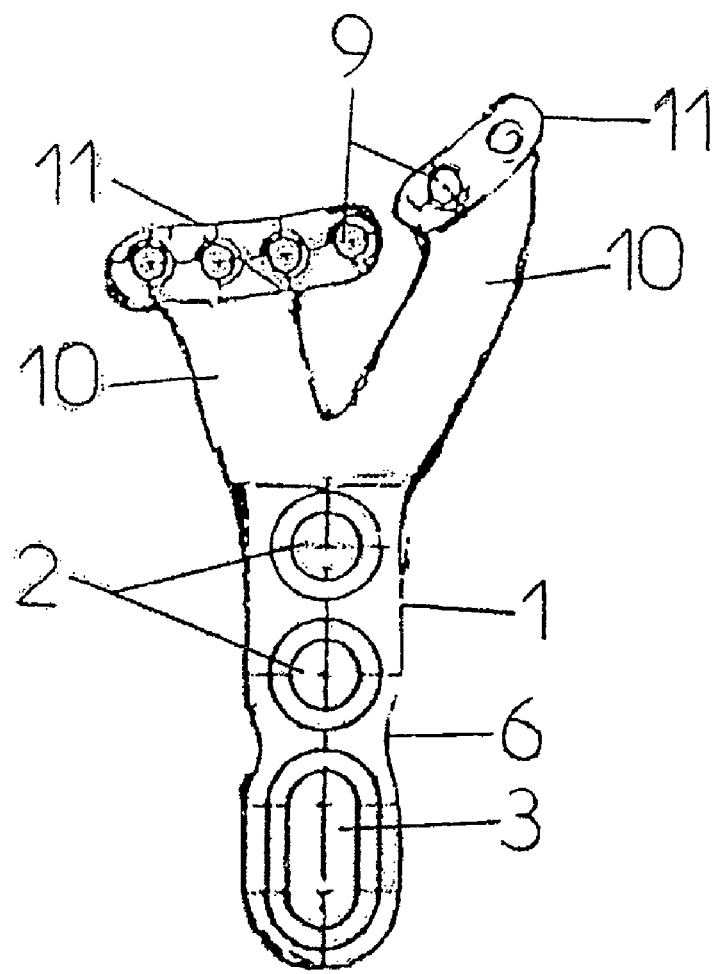

The radius plate according to FIG. 2 and 3 likewise comprises a shaft 1 having conical threaded bores 2 and an oblong hole 3 as well as a waisted recess 4. The basic form of this plate corresponds to a Y, however.

Thus, the side of the triangle away from the shaft 1 comprises a discontinuance or a free surface.

At the respective sides of the plate part 10 co-forming the Y-shape a transverse-surface section 11 is provided, respectively, wherein the transverse-surface sections 11 have a different length or width, as can be seen in FIG. 2

According to the illustration shown in FIG. 2 the longitudinal axes of the transverse-surface sections 11 include an angle or, according to FIG. 3, approximately correspond to a circular arc.

The side view onto the Y-plate part 10 according to FIG. 2 shows the anatomically adapted offset shape of the two finger-like legs of the Y-plate part 10. Here, too, the longitudinal axes of the threaded bores have a predominately non-parallel, i.e. angled position with respect to each other. The shape of the Y-plate part 10 allows a minor remodeling performance, depending on the type of fracture or the given fracture fragments, respectively.

The Y-shape moreover has the advantage that, in dorsal use, the tuberculum listeri, which is a bone protrusion, need not be removed.

In the embodiments according to the invention a fixed-angle screw joint is possible both in the area of the shaft 1 and the distal part 5 of the plate, i.e. near the interarticular space. Multi-fragment fractures may very well be fixed especially by choosing fixed-angle screws in the distal plate part with a diameter of substantially 2 mm. The embodiment of the radius plate according to FIG. 2 is based on a non-symmetrical Y-plate part configuration, wherein one leg of the plate part 10 is preferably shorter toward the shaft 1.

It is within the scope of the invention to vary the length of the transverse-surface sections 11 and the number of the conical smaller diameter bores 9 provided in the same.

The thickness of the plate material ranges substantially between 1 mm and 3 mm, wherein implant steel, titanium or a titanium alloy are used as material.

LIST OF REFERENCE NUMERALS 1 shaft
2 screw hole in the shaft
3 oblong hole
4 waisted recess
5 distal plate
6 right-angle bend
7 vault of the shaft
8 side of the plate away from the shaft
9 conical smaller diameter bore
10 Y-plate part
11 transverse-surface section

The invention claimed is:

1. A plate for stabilizing distal radius fractures, comprising:
 a longitudinal shaft; and
 a triangular plate part including a distal section provided at an end of the plate part farthest from the longitudinal shaft, first and second legs that each extend from respective ends of the distal section to an end of the longitudinal shaft, and a triangular envelope,
 wherein each of the first and second legs include respective inner and outer surfaces such that the respective inner surfaces extend from a center of the end of the longitudinal shaft to the respective ends of the distal section and the respective outer surfaces extend from peripheral surfaces of the end of the longitudinal shaft to the respective ends of the distal section,
 wherein the triangular envelope is defined by an interior surface of the distal section, the interior surface of the first leg, and the interior surface of the second leg,
 wherein the triangular envelope is scalene,
 wherein round holes are arranged in both the shaft and the distal section, the round holes including conical threaded bores with axes extending in a predominately non-parallel manner in the distal section,
 wherein a bend is disposed between the shaft and the triangular plate part,
 wherein a bore diameter of the round holes of the distal section is smaller than a diameter of the round holes of the longitudinal shaft,
 wherein an angle α is an angle between the longitudinal axes of the plurality of the conical threaded bores in the triangular plate part and a bottom surface of the longitudinal shaft, and
 wherein the angle a is a non-90° angle.

2. The plate according to claim 1 further comprising, an oblong hole disposed in the shaft.

3. The plate according to claim 1, wherein the cross-sectional area of the shaft includes a vault.

4. The plate according to claim 1, wherein corner surfaces of the triangular plate part are non-planar.

5. The plate according to claim 4, wherein the corner surfaces of the triangular plate part are curved.

6. The plate according to claim 1, wherein the threaded bores on the distal section approximately extend in a circular arc.

7. A plate for stabilizing distal radius fractures comprising:

a longitudinal shaft, and a plate part that includes first and second legs that respectively extend away from an end of the longitudinal shaft to define a Y-shape, wherein distal ends of the first and second legs include transverse surface sections that extend towards each other in an arc shape, wherein each of the first and second legs include respective inner and outer surfaces such that the respective inner surfaces extend from a center of the end of the longitudinal shaft to the respective transverse surface sections and the respective outer surfaces extend from peripheral surfaces of the end of the longitudinal shaft to the respective transverse surface sections, wherein a triangular envelope is defined by the interior surface of the first leg, the interior surface of the second leg, and the arc shape of the of the first and second transverse surface sections, wherein the triangular envelope is scalene, wherein round holes are arranged in both the shaft and the distal ends of the respective first and second transverse surface sections, wherein the round holes of the distal ends of the first and second transverse surface sections include conical threaded bores extending in a predominately non-parallel manner.

wherein a bend is disposed between the shaft and the plate part, and wherein a bore diameter of the round holes of the distal ends of the first and second transverse surface sections is smaller than a diameter of the round holes of the longitudinal shaft.

8. The plate according to claim 7, wherein the first and second transverse surface sections each include at least two threaded bores.

9. The plate according to claim 8, wherein the first transverse surface section has a different length than the second transverse surface section.

10. The plate according to claim 8, wherein an angle α is an angle between longitudinal axes of the threaded bores of the first and second transverse surface sections and a bottom surface of the longitudinal shaft.

11. The plate according to claim 1, wherein the longitudinal shaft includes two different widths.

12. The plate according to claim 1, wherein the bend disposed between the shaft and the triangular plate part includes an acute angle between a bottom surface of the triangular plate part and a plane that extends from a bottom surface of the longitudinal shaft towards the triangular plate part.

13. The plate according to claim 7, wherein the longitudinal shaft includes two different widths.

14. The plate according to claim 7, wherein the first and second transverse surface sections are dimensioned such that a bone protrusion fits between the distal ends of the first and second transverse surface sections.

15. The plate according to claim 14, wherein the bone protrusion is a tuberculum listeri.

16. The plate according to claim 7, wherein the bend disposed between the shaft and the plate part includes an acute angle between a bottom surface of the triangular plate part and a plane that extends from a bottom surface of the longitudinal shaft towards the plate part.

17. The plate according to claim 1, wherein the inner surface and the outer surface of the first leg are substantially parallel, and the inner surface and the outer surface of the second leg are substantially parallel.

18. The plate according to claim 7, wherein the inner surface and the outer surface of the first leg are substantially parallel, and the inner surface and the outer surface of the second leg are substantially parallel.

* * * * *